US012390507B1

(12) United States Patent
Anderson

(10) Patent No.: US 12,390,507 B1
(45) Date of Patent: Aug. 19, 2025

(54) METHOD TO PROVIDE CONSISTENT PRODUCT BATCHES ACTIVE COMPONENTS FOR ALKALOIDS OF KRATOM PLANTS

(71) Applicant: Michael Anderson, Delray Beach, FL (US)

(72) Inventor: Michael Anderson, Delray Beach, FL (US)

( * ) Notice: Subject to any disclaimer, the term of this patent is extended or adjusted under 35 U.S.C. 154(b) by 335 days.

(21) Appl. No.: 18/078,142

(22) Filed: Dec. 9, 2022

Related U.S. Application Data

(60) Provisional application No. 63/287,579, filed on Dec. 9, 2021.

(51) Int. Cl.
*A61K 36/74* (2006.01)
*A61K 9/50* (2006.01)

(52) U.S. Cl.
CPC ............ *A61K 36/74* (2013.01); *A61K 9/5073* (2013.01); *A61K 2236/15* (2013.01); *A61K 2236/17* (2013.01); *A61K 2236/333* (2013.01); *A61K 2236/51* (2013.01); *A61K 2236/53* (2013.01)

(58) Field of Classification Search
CPC .................. A61K 36/74; A61K 9/5073; A61K 2236/15; A61K 2236/17; A61K 2236/333; A61K 2236/51; A61K 2236/53
See application file for complete search history.

(56) References Cited

PUBLICATIONS

Beng et al, A Simple and Cost Effective Isolation and Purification Protocol of Mitragynine From *Mitragyna speciosa* Korth (Ketum) Leaves, 2011, vol. 15, No. 1, pp. 54-60. (Year: 2011).*

* cited by examiner

*Primary Examiner* — Trevor Love

(57) ABSTRACT

A method to produce a consistent product batch of Kratom plant active ingredients by isolating and separating the Kratom plant ingredients in prior processes and recombining the isolated ingredients in specify amounts for the final product. Encapsulating active ingredients together at different body internal release times to even out the active ingredient effects on the body over a time period to reduce highs and lows.

3 Claims, 2 Drawing Sheets

METHOD TO PROVIDE CONSISTENT PRODUCT BATCHES ACTIVE COMPONENTS FOR ALKALOIDS OF KRATOM PLANTS

CROSS REFERENCE TO RELATED APPLICATIONS

This application claims the benefit of provisional U.S. Patent Application Ser. No. 63/287,579 filed on Dec. 9, 2021

BACKGROUND OF THE INVENTION

Field of the Invention

This invention relates to a method for separation and isolation of the active components and alkaloids that come from the variety of kratom plants that provides for consistent product batches of active components when combined to specifically formulate the exact amount of each ingredient for a final product.

Being able to isolate and take different alkaloids/compounds from different strains including even one strain and formulate formulas for specific uses is critical for person/patient usage to know what each person/patient is really consuming and for what reasons.

Kratom is a type of tree that grows in the tropical climate of many countries throughout Southeast Asia. The leaves from the kratom trees are often dried in the sun and then ground into a fine powder, which can either be used by itself or in a capsule form.

Depending on how the kratom tree is grown and when its leaves are harvested, the resulting kratom powder will have distinct physical and physiological characteristics. These characteristics determine the "strain" of kratom, which is usually identified with a color and with a region of origin. The different strains and different alkaloids are dependent on weather, geographic location, soil conditions to mention a few. It is not possible to have a standard formula with one or more specific alkaloids to be precise on every dose as the percentages change from leaf to leaf and plant to plant. This invention will allow for the first time to have a standard for dosing so the patient/person knows each time that they are getting exactly the same dose and effect each time and not wondering if they took too much or too little from batch to batch.

Knowing which kratom strains there are and how each works is key to finding the best kratom strain.

RELATED PRIOR ART

A large majority of KRATOM and or KRATOM products manufactured ranging from pain cream, acne gels, tinctures, capsules, sprays, vapes, candies, shatter (butane hash oil), chocolates, tonics and gummy bears, just to name a few, use and isolate just the KRATOM molecule and do not contain any other KRATOM or other KRATOM compounds such as mitragynine, 7-hydroxymitragynine (7-HMG), speciociliatine, corynantheidine, speciogynine, paynantheine, mitraphylline, rhynchophylline, mitralactonal, raubasine, and mitragynaline and so on, further described more in depth, in this invention, just pure isolated KRATOM, ranging in purity from 92 percent to 99 plus percent. It is semi-easy to deal with as there is no KRATOM or other compounds and usually is much less expensive. Most chemists, scientists, formulators and manufacturers, including those who are in the business, know that full spectrum and broad spectrum KRATOM, with or without a portion being KRATOM, is more valuable and diverse than just the KRATOM alone and has many more benefits.

Besides the higher cost, in full or broad spectrum, with or without KRATOM, is the problem of having a consistent product, batch after batch. It is virtually impossible to extract the oil and have the oil the same every time. The result is the KRATOM product is not marketable to large companies, as each batch is not the same, which means that every formula can deviate greatly and cannot not be an effective or reliable dose.

The present invention completely eliminates any variables that are found in today's concerns of percentages of different compounds/ingredients in a full and or broad spectrum of more than one ingredient and compound found in the plant of Kratom. This invention also relates if the alkaloids are synthesized, to specific alkaloid compounds/ingredient and dosage levels. This invention is not limited to the Kratom species, as the same can be applied for any other species of living or nonliving commodities and or products. Below, here within is a further explanation of the invention.

SUMMARY OF THE INVENTION

KRATOM CONSISTENT FORMULAS: *Mitragyna speciosa* (commonly known as kratom) is a tropical evergreen tree in the coffee family native to Southeast Asia. It is indigenous to Thailand, Indonesia, Malaysia, Myanmar, and Papua New Guinea, where it has been used in herbal medicine since at least the nineteenth century.

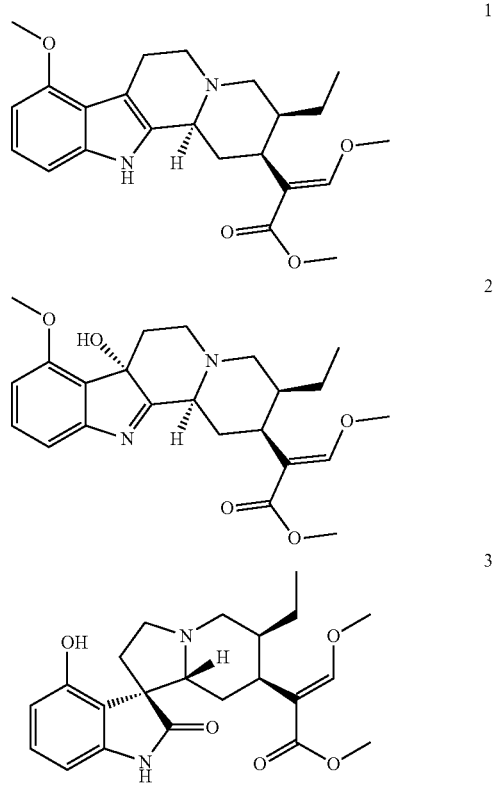

Structures of selected alkaloids present in kratom (*Mitragyna speciosa*), mitragynine (1), 7-hydroxmitragynine (2) and speciofoline (3).

Mitragynine
$C_{23}H_{30}N_2O_4$, MW 398.5

Speciogynine
$C_{23}H_{30}N_2O_4$, MW 398.5

Paynantheine
$C_{23}H_{28}N_2O_4$, MW 396.48

Speciociliatine
$C_{23}H_{28}N_2O_4$, MW 396.48

This invention relates to a method to produce consistent product batches for a final product that is based on active ingredients and compounds that come from the kratom plant. There are compounds found in the plants that include, but are not limited to, Kratom. Kratom contains at least 54 alkaloids. These include mitragynine, 7-hydroxymitragynine (7-HMG), speciociliatine, corynantheidine, speciogynine, paynantheine, mitraphylline, rhynchophylline, mitralactonal, raubasine, and mitragynaline.

Mitragynine:
Indole alkaloid. Analgesic, antitussive, antidiarrheal, adrenergic, antimalarial, possible psychedelic (5-HT2A) antagonist. Mitragynine is the primary alkaloid in kratom, and is believed to be responsible for the majority of its effects. Roughly 66% of total alkaloid content found in kratom leaf.

Paynantheine:
Indole alkaloid. Appears to be a smooth muscle relaxer, but there is limited research available and more needs to be done. 8.6% to 9% of total alkaloid contents in Kratom leaf. Second most abundant alkaloid.

Mitraphylline:
Oxindole alkaloid. Vasodilator, antihypertensive, muscle relaxer, diuretic, antiamnesic, anti-leukemic, possible immunostimulant. <1% of total alkaloid contents in Kratom leaf.

Isomitraphylline:
Immunostimulant, anti-leukemic. <1% of total alkaloid content found in Kratom leaf.

Speciogynine
Diastereomer of mitragynine. Possible smooth muscle relaxer. 6.6% to 7% of total alkaloid contents of kratom leaf, representing the third most abundant alkaloid.

Akuammigine:
An indole alkaloid associated with the seeds of *Picralima nitida* (akaumma). It is structurally similar to yohimbine and mitragynine. Like yohimbine, it is known to have antimalarial activity.

Rhynchophylline:
Vasodilator, antihypertensive, calcium channel blocker, antiaggregant, anti-inflammatory, antipyretic (fever reducing), antiarrhythmic, and anthelmintic (treatment of parasitic worms). It is a also non-competitive NMDA antagonist, and appears to also have effects on dopamine and 5-HT receptors. Chinese Cat's claw (*Uncaria tomentosa*) has also been found to contain rhynchophylline. It has a similar chemical structure to mitragynine, and represents <1% of total alkaloid content found in kratom leaf.

Ajmalicine (Raubasine):
Cerebrocirculant, antiaggregant, anti-adrenergic (at alpha-1), sedative, anticonvulsant, smooth muscle relaxer. It's structurally related to alkaloids from yohimbe. Ajmalicine is an α1-adrenergic receptor antagonist with preferential actions over α2-adrenergic receptors, which is the reason for its hypotensive effects. According to 'Alkaloids: Biochemistry, Ecology, and Medical Applications', ajmalicine "depletes peripheral noradrenaline stores, resulting in a decrease of peripheral resistance and blood pressure. It also causes depletion of catecholamine and serotonin stores in the brain, heart, and many other organs". Ajmalicine is also found in *Rauwolfia serpentina.*

Isorhynchophylline
Immunostimulant, and possible antihypertensive and neuroprotective. <1% of total alkaloid content found in Kratom leaf.

Ciliaphylline:
Antitussive, analgesic. <1% of total alkaloid content found in Kratom leaf.

Corynantheidine (Rauhimbine):
μ-opioid antagonist, also found in Yohimbe. It's related to ajmalicine, and is a diastereomer of yohimbine. Like ajmalicine, it is an α1-adrenergic and α2-adrenergic receptor antagonist with 10× greater affinity for the α1-adrenergic receptor. This is in contrast to yohimbine and its other diastereomer, rauwolscine, which have a 30× higher affinity for the α2-adrenergic receptor over the α1-adrenergic (opposite affinities). <1% of total alkaloid content found in Kratom leaf.

Corynoxeine:
Calcium channel blocker. <1% of total alkaloid content found in Kratom leaf.

Corynoxine A and B:
Dopamine mediating anti-locomotives, meaning that they act as somewhat of a sedative. They are also found in Chinese Cat's Claw (*Uncaria tomentosa*). There is also some research that suggests they may help with Parkinson's. <1% of total alkaloid content found in Kratom leaf.

Epicatechin:

A flavonoid that is an antioxidant, antiaggregant, antibacterial, antidiabetic, antihepatitic, anti-inflammatory, anti-leukemic, antimutagenic, antiperoxidant, antiviral, potential cancer preventative, alpha-amylase inhibitor. One preliminary study even claims that it may reduce myostatin, which would result in muscle growth and improved strength. It's also found in dark chocolate, green tea, and grapes.

9-Hydroxycorynantheidine:

Partial opioid agonist. One study found that "9-Hydroxycorynantheidine inhibited electrically stimulated guinea-pig ileum contraction, but its maximum inhibition was weaker than that of mitragynine and its effect was antagonized by naloxone, suggesting that 9-hydroxycorynantheidine possesses partial agonist properties on opioid receptors"

Isomitrafoline:

<1% of total alkaloid content found in Kratom leaf.

Isopteropodine:

Immunostimulant, antimicrobial.

Isospeciofoline:

1% of total alkaloid content found in Kratom leaf. Mitraciliatine:

<1% of total alkaloid content found in Kratom leaf.

Mitragynine Oxindole B.

<1% of total alkaloid content found in Kratom leaf.

Mitrafoline:

<1% of total alkaloid content found in Kratom leaf.

Mitraversine:

Found in *Mitragyna parvifolia*, and may also be in *Mitragyna speciosa*

Speciociliatine:

Diastereomer (C3 stereoisomer) of mitragynine. Weak opioid agonist. May inhibit acetylcholine release from presynaptic nerve through means other than opioid receptor stimulation. 0.8% to 1% of total alkaloid content of kratom leaf. Unique to Kratom.

Speciofoline:

Potential analgesic and antitussive. Patented (U.S. Pat. No. 3,324,111) by Smith Kline (of Glaxo Smith Kline) in 1964. Also patented (US20100209542) by the University of Massachusetts Medical School and University of Mississippi in 2009 to treat opiate withdrawal. As of Feb. 18, 2019, the patent is listed as abandoned.

Tetrahydroalstonine:

Hypoglycemic, anti-adrenergic (at alpha-2), some as shown in some figures provided herein but not limited to.

Terpenes and terpenoids are compounds that are in the kratom plant. There has been reportedly over 80 to over 200 or more terpenes that kratom plants can produce and can vary greatly, depending on the strains, soil conditions, age, water/moisture amounts and sunlight and strains and genetics. There are over 80 cannabinoids in certain species of plants; so the compounds can be vast, which is another critical reason for this invention.

It is impossible to have consistency of more than one compound, without adding each separate compound/ingredient(s) to a formula, to make the compound a standard or constant exact dose for mass production of a drug or nutritional product. By adding each compound or ingredient(s), individually, consistency results on each batch produced for assured quality.

The process and manufacturing of the separated, individual compounds depends on converting, as an example, Kratom that is done, by heat or not, and depending on the extraction or manufacturing process, that consist of heat variables or not. When heated, the conversion happens, but both separately are important to a body in their own ways depending on the procedure and or ingredients used along with different machines for separation/isolation of compounds. Terpenes are also very important molecules that can be used by heat conversion in both ways as well. Whether it is, Kratom or the Kratom family, every time separately manufactured/extracted or in different ratios, is thus not allowing for the same product.

1. Extraction methods including but not limited to by any means:

All the extractions were performed using a 1:10 plant to solvent ratio. Dried leaves were pulverized in a plant blender (Blendor, Warig Commercial) at a size range of 300-400 m before extraction.

The solvents which were employed for the extractions were: MeOH (met), EtOH (et), MeOH:H2O 1:1 (met/w), EtOH:H2O 5:95 pH 3 (et/w, pH adjusted with HCl 1 M.

2. Conventional Heating Extraction Procedure

Fifty gram of powdered leaves were added to 500 mL of solvent and the mixture was heated at 50° C. for 3 h, then cooled down and filtered twice on gauze and filter paper. The solvent was removed under vacuum.

3. Five grams of powdered leaves, were soaked in 50 mL of solvent (met or met/w or et/w pH 3) and sonicated at room temperature for 1 h using an immersion titanium horn (21.4 kHz, 70 W). During the extraction the temperature was monitored and kept constant (25° C.±1) using a thermostated bath. The final mixture was filtered twice on gauze and filter paper and the solvent was removed under vacuum.

Five grams of dried powdered leaves were soaked in 50 mL of solvent (met, met/w or et/w pH 3) and sonicated at room temperature for 1 h using a high-power US-bath (19.6 kHz, 50 W). During the extraction the temperature was monitored and kept constant (25±1) with an external cold water flow. The final mixture was filtered twice on gauze and filter paper and the solvent was removed under vacuum.

4. A mixture of dried crushed leaves (2 g) and solvent (20 mL) (C) was irradiated in a pressure resistant vessel in the MW oven (110° C., average power 60 W) for 1 h. The final mixture was then cooled down and filtered twice on gauze and filter paper. The solvent was removed under vacuum.

5. Two hundred and forty-three grams of leaves powder were extracted using 28.8% EtOH as a co-solvent, at 65° C., 300 bar, 12 kg/h of CO2 flow, for 45 min. The ethanol extract was collected and evaporated under vacuum.

6. The crude dried extracts were suspended in water and the pH was adjusted to 3 with 0.1 M hydrochloric acid, the mixtures were then washed with petroleum ether. A 0.1 M solution of NH4OH was added to the aqueous layer until pH 9 was reached and the alkaloids were extracted with dichloromethane. The organic phase was dried over anhydrous Na2SO4 and the solvent removed under vacuum.

7. An aliquot (200 mg) of alkaloid extract was purified by flash chromatography, using petroleum ether (A) and ethyl acetate (B) as binary eluents, on a 4 g silica gel column (flow rate 18 mL/min and UV detection 254 nm). The elution gradient was programmed as follows: (min, B %) 0, 10; 5, 10; 7, 15; 12, 15; 19, 30; 31, 30; 35, 50; 36, 100; 37, 100. Fractions were analyzed by GC-MS on Agilent 6890, Agilent Technologies—USA, equipped with Agilent Network 5973 mass detector. A 30 m capillary column (HP-5MS, 5% phenyl methyl siloxane, i.d. of 0.25 mm and film thickness 0.25 m) was used with flow of 1.2 mL/min (GC parameters: initial temp. 80° C.; rate 10° C./min, final temp. 150° C., hold 4 min; rate 10° C./min, final temp. 300° C., hold 10 min; split ratio 20:1, temp. 250° C.; MS parameters: low mass 40, high mass 800, MS quad 150° C., MS source 230° C.). The identification of products was achieved using the NIST 05 library (National Institute of Standards and Technology). Fractions containing mitragynine were collected and the solvent was removed under vacuum. Purity of the obtained mitragynine was estimated, by comparison of GC peak areas, in 94.17%.

Taking the ingredients as mentioned herein, and others if ingredients that are separated, then mixed according to ratios or by weight to a predetermined formula and manufacturing process, the exact same full or broad spectrum KRATOM and Terpene formula heated and no heated depending on what you want in the finished formula, can be created. Now consistent formulas can be created with over a 99 percent or higher ratio and be able to formulate many specific formulas in any combination of the above mentioned ingredients, including adding other nutritional and or pharmaceutical ingredients.

There are many ailments and health disorders and diseases that KRATOM and other ingredients help treat and now can be specifically formulated for the exact amount of each ingredient required for a final product, whether for humans or animals, for ingesting, injections, or topical products for example, but not limited to, that help treat Parkinson, Alzheimer's, Seizures, Pain and inflammation to mention a few.

KRATOM, Terpenes and other family of compounds found in Kratom plants and its family of plants has been shown to help in diseases and symptoms such as anxiety, psoriasis, cancer, MS, nausea, chronic pain, seizures/epilepsy, anxiety, psoriasis, diabetes, PTSD, strokes just to mention a few that includes KRATOM and compounds as well as terpenes and their compounds.

It is an object of this invention to provide a method of producing consistent formulas of active ingredients from Kratom plants and Terpenes for consistent product batches when combined of KRATOM and Terpenes when combined to formulate specific ingredients in a final product.

DESCRIPTION OF PREFERRED
EMBODIMENTS OF THE INVENTION

Figure 1:
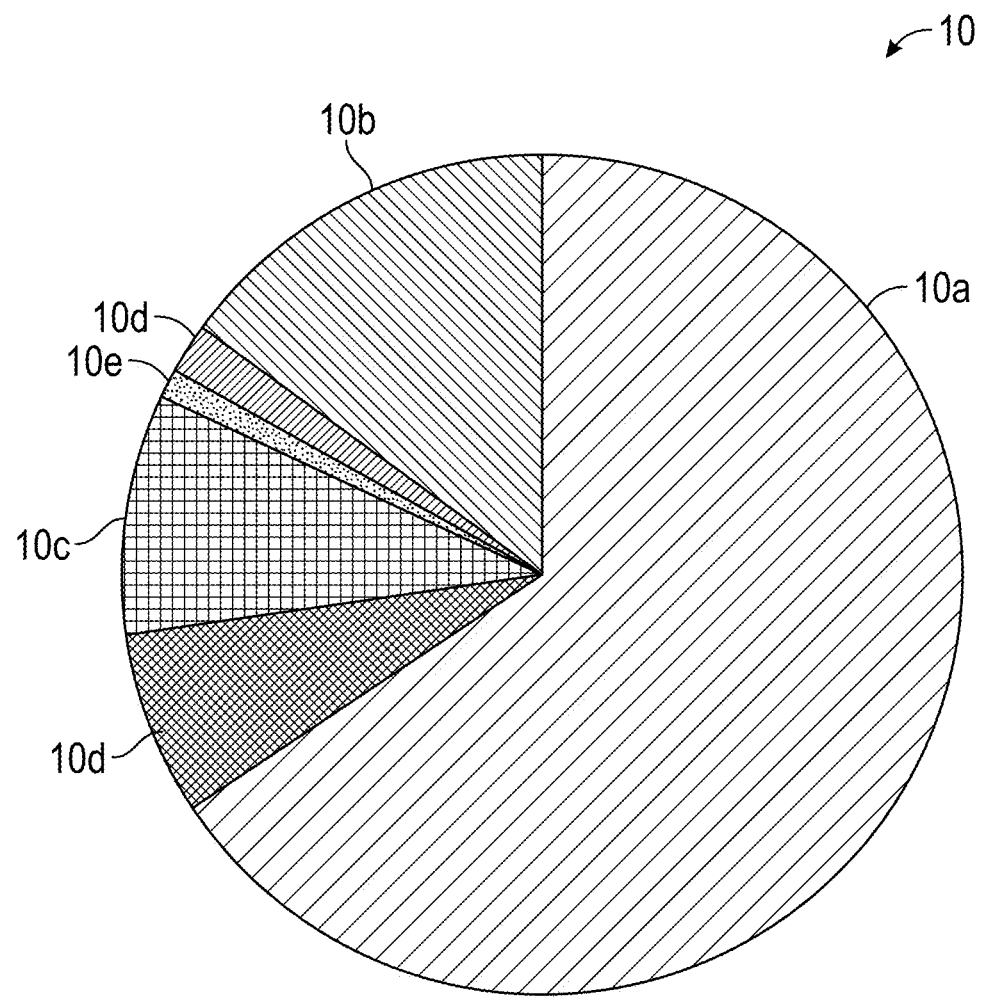
FIG. 1, shows a chart of estimate Thai kratom extract composition ingredients.

FIG. 1 shows a chart of Thai kratom extract composition ingredients.

An example below for a formula, for end product consistency, add 1 milligram of each of the following previously isolated, separated components/compounds/ingredients in a prior separation/extraction process, to provide, for the first time, a consistent final product formula on an ongoing basis, without deviation and with complete consistency, including adding other drugs, medicines and or nutraceuticals of any kind. The following is only an example to show the invention is critical and cannot be done without the invention process, if a formula needed to be 1 milligram of each:

Mitragynine, 7-hydroxymitragynine (7-HMG), specio-ciliatine, corynantheidine, speciogynine, paynantheine, mitraphylline, rhynchophylline, mitralactonal, raubasine, and mitragynaline.

Figure 2A:
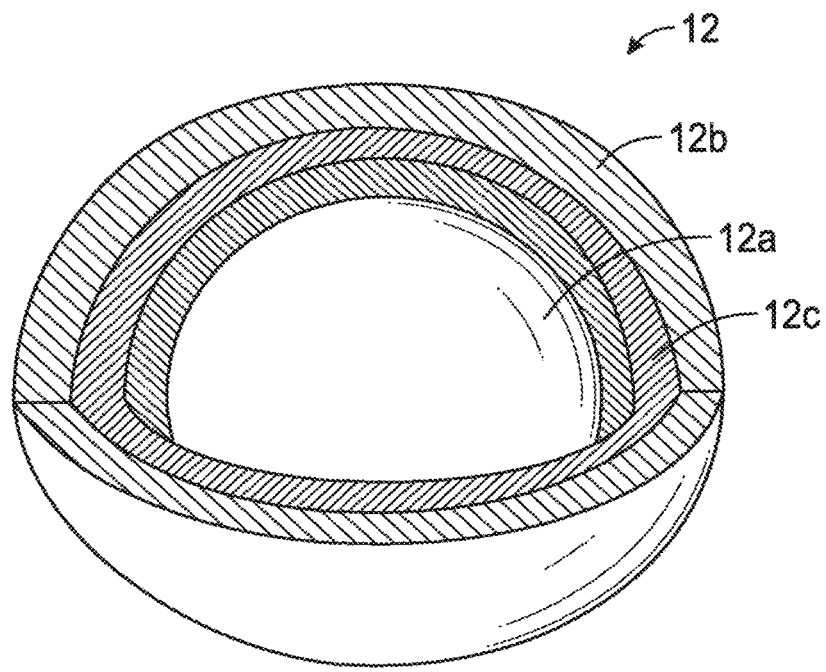
FIG. 2a shows a cutaway diagram of encapsulated active ingredient.
Figure 2B:
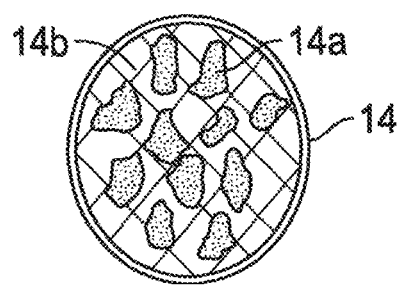
FIG. 2b shows a microcapsule and core containing active ingredient.
Figure 2C:
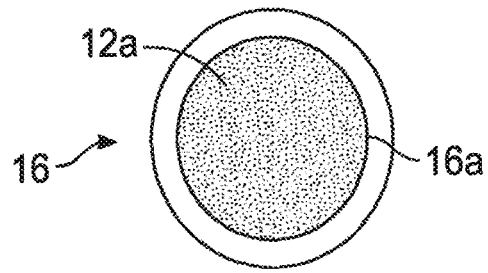
FIG. 2c shows a microsphere with polymer network and dispersed active compound.

Another embodiment of the present invention provides a time release/extended release composition comprising certain ingredients that can be provided that are from Evonics and Colorcon among other companies, ingredients that can provide coating materials, including other ingredients that can be used in itself or part of such as dextrin's, starch and chitosan. FIGS. 2a, 2b, and 2c show the substance that is encapsulated which may be called the core material, the active agent, fill, internal phase, or payload phase. And the substance that is encapsulating may be called the coating, membrane, shell, carrier material, wall material, capsule, external phase, or matrix. FIG. 2a shows a nutrient core material 12a. encapsulation layer 12b, and encapsulation layer 12c. FIG. 2b shows a microsphere 14 that includes a polymer network 14b, and a dispersed active compound 14a. FIG. 2c shows a microcapsule 16 having a membrane 16a with capsule core containing active material 12a.

Thereof one or more nutra and/or pharma excipients that are for multi hour release of active materials, instead of all at once. Manufacturing can be done in a coating pan, fluid beds, and among other types of spray drying techniques to provide a controlled release pattern that can be layered with multiple coatings and multiple coating ingredients, depending on the release of what is desired, to protect against moisture, to help in odor and taste reduction, and to making oil into water soluble products.

Furthermore, specific coating materials can be used so that certain active ingredient(s) will only dissolve/enter into the blood stream in specific areas of the body such as stomach, large intestine, duodenum and lleum. With this technique with certain minerals, vitamins, herbs and or drugs, the amount of actives used can be much less than a standard dose due to releasing, specifically including time release over time, of the active ingredient(s). There are many formulas that can be done by this invention, and below are some examples, but are not limited to the examples, as there are limitless combinations that now can be done based on this invention.

Encapsulation Example 1

100 mg caffeine, 100 mg taurine, 20 mg niacin, 50 mg potassium, 5 mg magnesium, 1 mg kratom, and 30 mg of calcium every hour over a period of 7 hours.

Encapsulation Example 2

2 mg melatonin, 30 mg valerian root, 35 mg 1-tryptophan, 15 mg gaba, 1 mg KRATOM, 1 mg CBG.

Encapsulation Example 3

1 mg of kratom either isolate, full spectrum or broad spectrum, 1 mg CBG and or any amounts of terpenes or any single or any combination thereof, release every hour on the hour for a period of 8 hours or any amount of hours desired.

With this invention there are unlimited amounts of new medicines that are manmade/synthetic or by nature that have enormous applications to the body and market. Having ingredients release overtime is the most efficient way of obtaining the highest bioavailability possible to any human or animal.

Furthermore the ingredients/compounds can be microencapsulated for specific time release, targeted release, making water soluble oil to odor and taste masking that can be crucial for specific formulas.

The invention claimed is:

1. A method of producing a consistent final product formula for Kratom plants including the steps of:
    Isolating and separating each Kratom plant ingredients into a separate ingredient in a prior separation process; and
    Recombining each of the ingredients in consistent measured amounts to make up the final product.

2. The method as in claim 1, including the step of:
    Providing a time release coating on said final product of claim 1.

3. The method as in claim 1, wherein:
    Each ingredient is a separated one milligram.

* * * * *